(12) United States Patent
Fujiwara

(10) Patent No.: US 11,262,573 B2
(45) Date of Patent: Mar. 1, 2022

(54) ENDOSCOPE LIGHT-SOURCE DEVICE

(71) Applicant: OLYMPUS CORPORATION, Hachioji (JP)

(72) Inventor: Kazuto Fujiwara, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 17/117,399

(22) Filed: Dec. 10, 2020

(65) Prior Publication Data

US 2021/0088773 A1    Mar. 25, 2021

Related U.S. Application Data

(63) Continuation of application No. PCT/JP2019/006693, filed on Feb. 22, 2019.

(30) Foreign Application Priority Data

Jul. 18, 2018 (JP) .............................. JP2018-134878

(51) Int. Cl.
*G02B 23/24* (2006.01)
*G02B 27/10* (2006.01)
*G02B 6/42* (2006.01)
*A61B 1/07* (2006.01)
*A61B 1/06* (2006.01)

(52) U.S. Cl.
CPC ........ *G02B 23/2469* (2013.01); *A61B 1/0661* (2013.01); *A61B 1/07* (2013.01); *G02B 6/42* (2013.01); *G02B 23/2407* (2013.01); *G02B 27/10* (2013.01)

(58) Field of Classification Search
CPC ............ G02B 23/2469; G02B 23/2407; G02B 23/2461; G02B 6/42; G02B 27/10; A61B 1/0661; A61B 1/07
See application file for complete search history.

(56) References Cited

U.S. PATENT DOCUMENTS

| | | | | |
|---|---|---|---|---|
| 5,508,846 | A * | 4/1996 | Hall | ................... G02B 13/0045 250/214 VT |
| 6,768,593 | B1 | 7/2004 | Jutamulia | |
| 9,046,672 | B2 * | 6/2015 | You | ..................... G02B 13/0045 |

(Continued)

FOREIGN PATENT DOCUMENTS

| | | |
|---|---|---|
| JP | H10111438 A | 4/1998 |
| JP | 2005342034 A | 12/2005 |

(Continued)

OTHER PUBLICATIONS

International Search Report (ISR) (and English translation thereof) dated May 21, 2019 issued in International Application No. PCT/JP2019/006693.

*Primary Examiner* — William N Harris
(74) *Attorney, Agent, or Firm* — Holtz, Holtz & Volek PC

(57) ABSTRACT

An endoscope light-source device includes a semiconductor laser light source, a first lens group that diverges a low-NA light component of light from the semiconductor laser light source and converges or collimates a high-NA light component of the light from the semiconductor laser light source, and a second lens group that focuses the light passing through the first lens group onto an end surface of a light guide. The first lens group includes at least one aspherical lens.

6 Claims, 19 Drawing Sheets

(56) References Cited

U.S. PATENT DOCUMENTS

| | | | |
|---|---|---|---|
| 9,784,951 B2* | 10/2017 | Ichimura | G02B 13/04 |
| 2004/0051956 A1* | 3/2004 | Suzuki | G02B 3/04 |
| | | | 359/641 |
| 2014/0005483 A1 | 1/2014 | Ohashi et al. | |
| 2016/0324420 A1 | 11/2016 | Zhu et al. | |

FOREIGN PATENT DOCUMENTS

| | | |
|---|---|---|
| JP | 2013043027 A | 3/2013 |
| JP | 2014008316 A | 1/2014 |
| WO | 2015105951 A1 | 7/2015 |

* cited by examiner

US 11,262,573 B2

ENDOSCOPE LIGHT-SOURCE DEVICE

CROSS-REFERENCE TO RELATED APPLICATIONS

This is a continuation of International Application PCT/JP2019/006693, with an international filing date of Feb. 22, 2019, which is hereby incorporated by reference herein in its entirety.

This application is based on Japanese Patent Application No. 2018-134878, the content of which is incorporated herein by reference.

TECHNICAL FIELD

The present invention relates to endoscope light-source devices.

BACKGROUND ART

A known endoscope light-source device uses a concave lens to diverge light emitted from a semiconductor laser light source (referred to as "LD light source" hereinafter), subsequently converges the light by means of a convex lens, and causes the light to enter a light guide (e.g., see Patent Literature 1).

CITATION LIST

Patent Literature

{PTL 1}
Japanese Unexamined Patent Application, Publication No. 2013-43027

SUMMARY OF INVENTION

An aspect of the present invention is directed to an endoscope light-source device including a laser light source, a first lens group that diverges a low-numerical-aperture light component of light from the laser light source and converges or collimates a high-numerical-aperture light component of the light from the laser light source, and a second lens group that focuses the light passing through the first lens group onto an end surface of a light guide. The first lens group includes at least one aspherical lens.

DESCRIPTION OF EMBODIMENTS

An endoscope light-source device 1 according to a first embodiment of the present invention will be described below with reference to the drawings.

Figure 1:
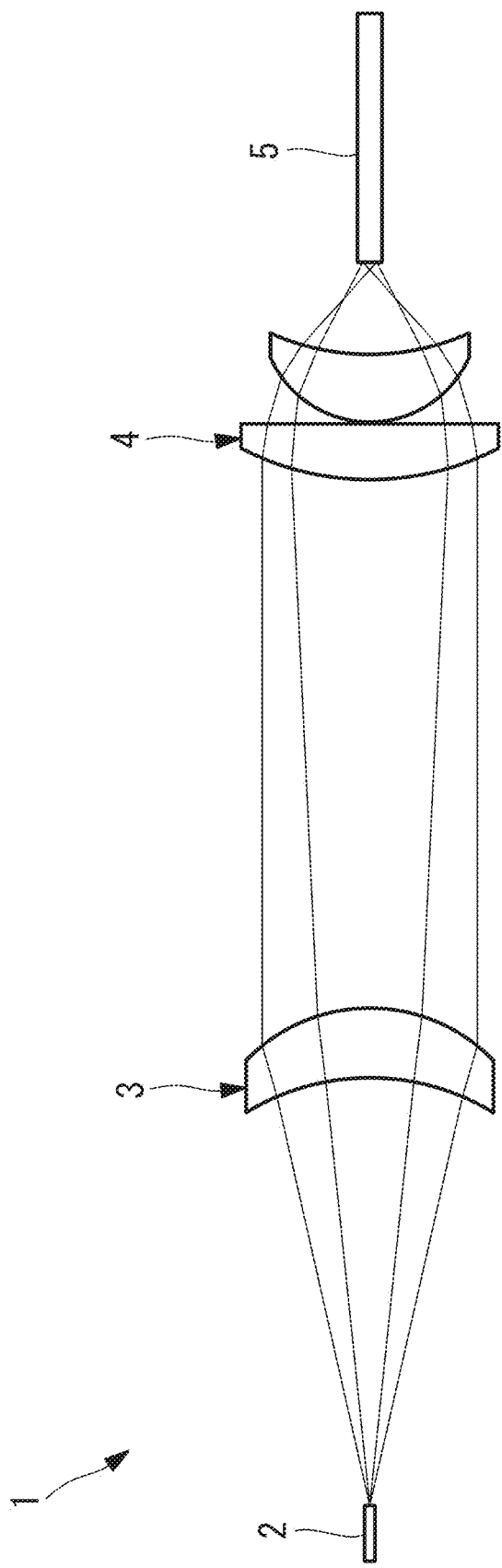
FIG. 1 schematically illustrates an endoscope light-source device according to an embodiment of the present invention.

As shown in FIG. 1, the endoscope light-source device 1 according to this embodiment includes a semiconductor laser light source 2 that emits laser light, a first lens group 3 that allows the laser light emitted from the semiconductor laser light source 2 to pass therethrough, and a second lens group 4 that focuses the laser light passing through the first lens group 3.

The first lens group 3 is constituted of a single aspherical lens. The aspherical lens has a curvature such that the power at the most peripheral area is higher than the power on the optical axis.

In more detail, the semiconductor laser light source 2 and the first lens group 3 satisfy conditional expressions (1) and (2) indicated below.

$$5 \text{ mm} \leq NA/\varphi2 \leq 25 \text{ mm} \tag{1}$$

$$1/\varphi2 \leq L < 1/\varphi1 \tag{2}$$

where NA denotes the numerical aperture of the semiconductor laser light source 2, φ1 denotes the power of the first lens group 3 on the optical axis, φ2 denotes the power of the first lens group 3 at the most peripheral area, and L denotes the distance between the semiconductor laser light source 2 and the principal point of the first lens group 3.

Accordingly, of the laser light from the semiconductor laser light source 2, the first lens group 3 diverges a laser light component with a low NA and converges or collimates a laser light component with a high NA. The end surface of a light guide 5 provided in the endoscope is disposed at the focal point of the laser light focused by the second lens group 4, so that the laser light focused by the second lens group 4 is made to enter the light guide 5 and can be output from the distal end of the endoscope.

In more detail, the second lens group 4 satisfies conditional expression (3) indicated below.

$$5 \text{ mm} \leq NA'/\varphi3 \leq 25 \text{ mm} \tag{3}$$

where NA' denotes the numerical aperture of the light guide 5, and φ3 denotes the power of the second lens group 4.

The operation of the endoscope light-source device 1 according to this embodiment will be described below.

In the endoscope light-source device 1 according to this embodiment, the laser light emitted from the semiconductor laser light source 2 spreads in accordance with the numerical aperture NA of the semiconductor laser light source 2, passes through the first lens group 3, and subsequently passes through the second lens group 4, so as to be focused onto the end surface of the light guide 5.

Figure 2:
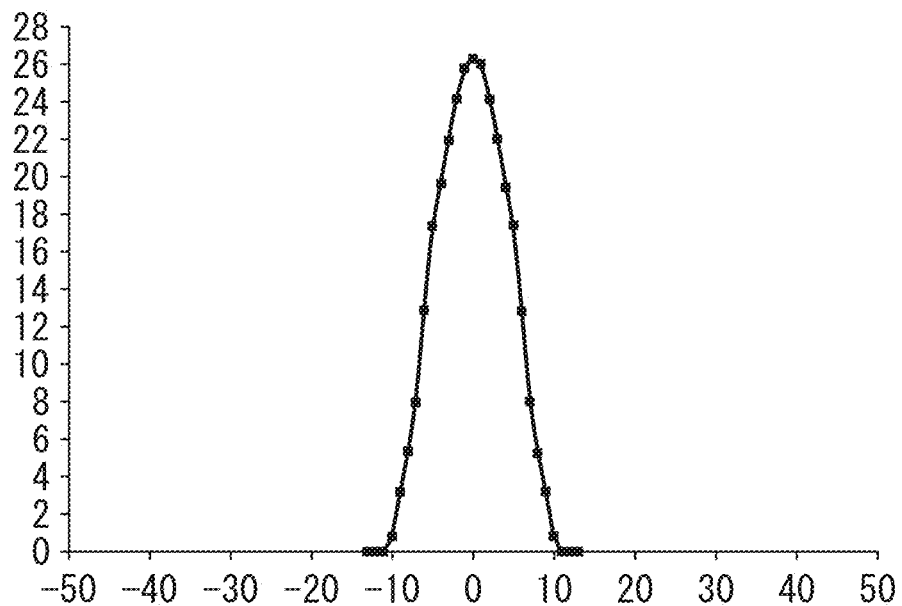
FIG. 2 illustrates a light distribution of a semiconductor laser light source provided in the endoscope light-source device in FIG. 1.
Figure 3:
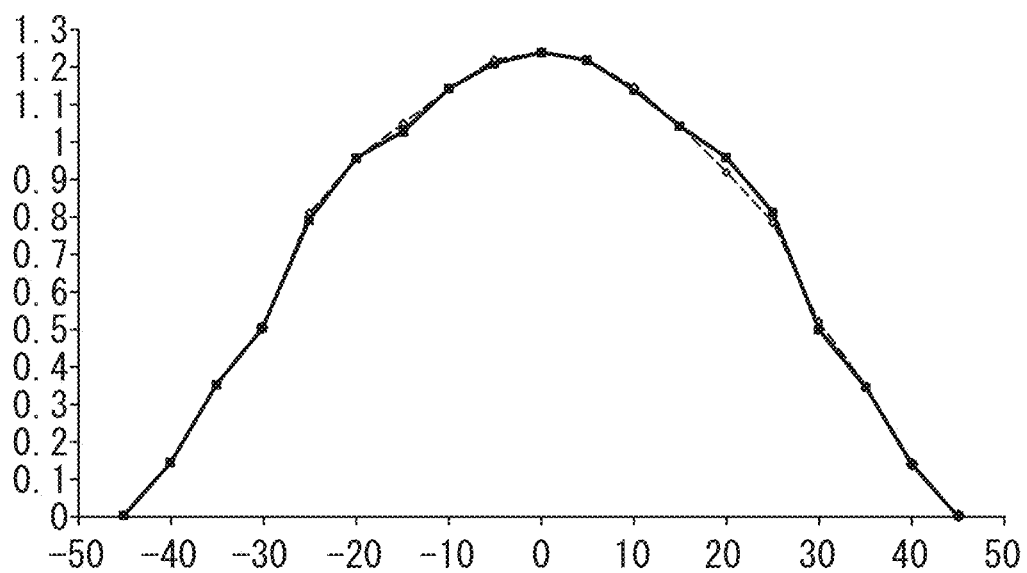
FIG. 3 illustrates a light distribution of illumination light emitted from the endoscope light-source device in FIG. 1.

In this case, in the endoscope light-source device 1 according to this embodiment, the low-NA laser light component of the laser light from the semiconductor laser light source 2 having a narrow light distribution, as shown in FIG. 2, is increased in beam diameter by being diverged by the first lens group 3, and is subsequently focused by the second lens group 4. Accordingly, a wide light distribution can be obtained, as shown in FIG. 3.

Figure 4:
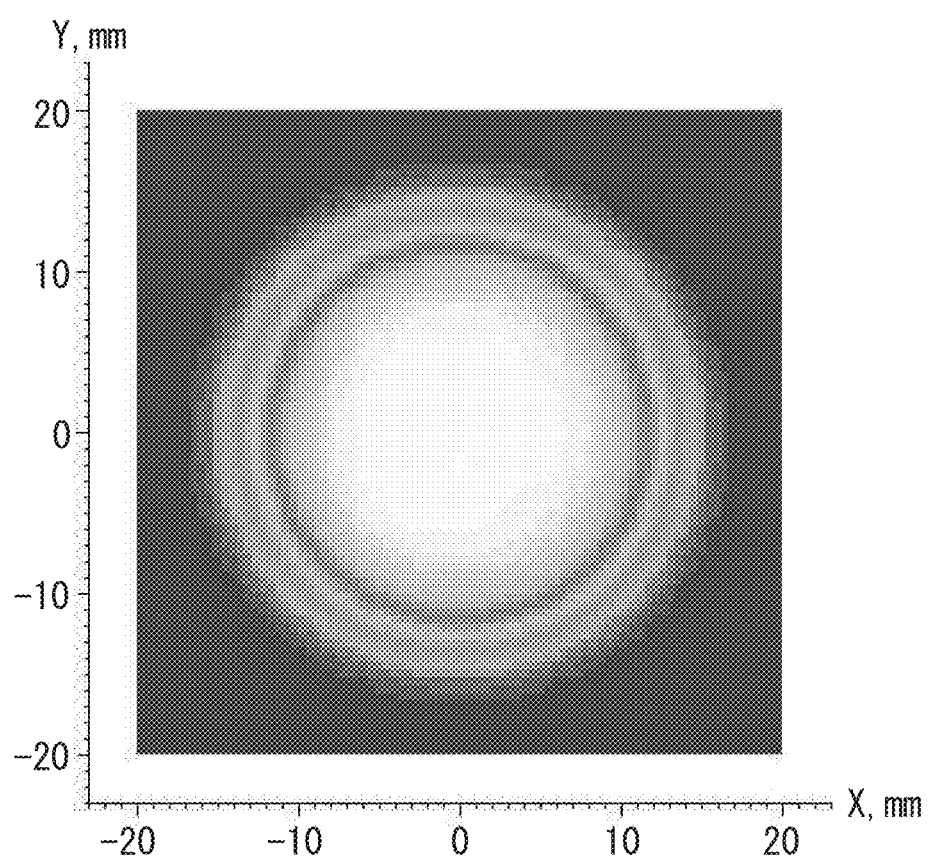
FIG. 4 illustrates an intensity distribution of illumination light between lenses in FIG. 1.

On the other hand, the high-NA laser light component of the laser light from the semiconductor laser light source 2 would have an excessively large beam diameter if it were diverged similarly to the low-NA laser light component by the first lens group 3, thus causing vignetting to occur due to the second lens group 4. This embodiment is advantageous in that the high-NA laser light component is converted into collimated light by the first lens group 3 and is subsequently focused by the second lens group 4, thereby preventing vignetting and reducing a loss in light quantity. Accordingly, illumination light with the intensity distribution in the XY directions shown in FIG. 4 can be output from the distal end of the endoscope.

This embodiment is advantageous in that it can obtain illumination light with a sufficiently wide light distribution without reducing the light quantity.

Figure 5:
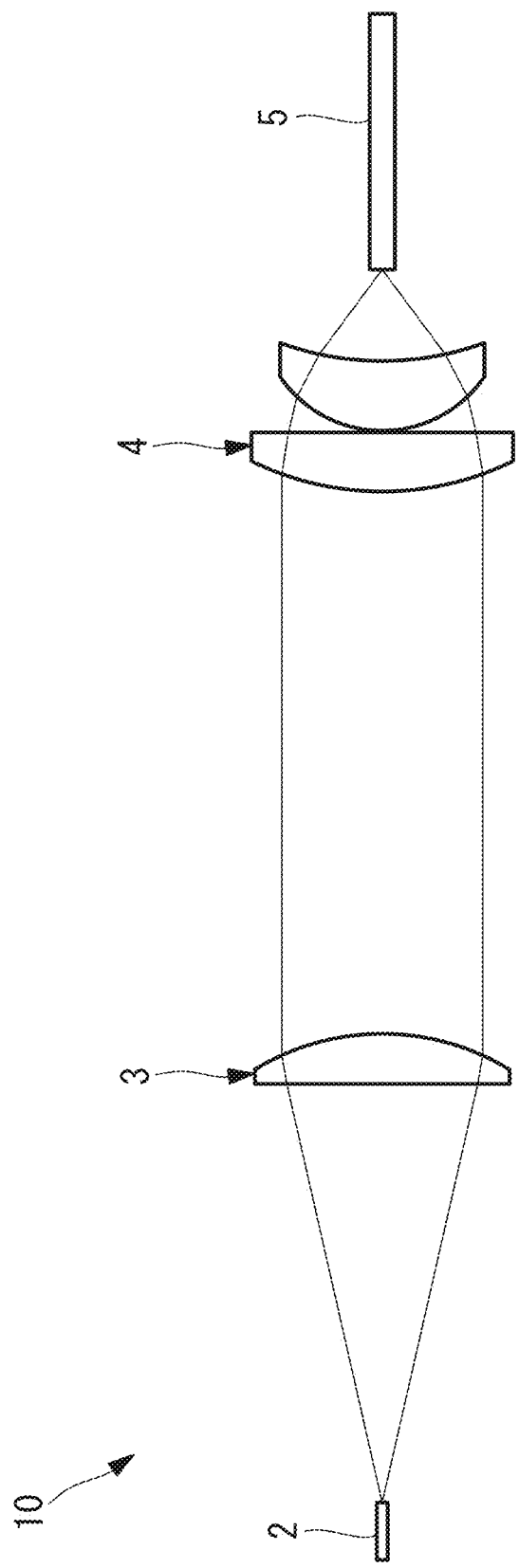
FIG. 5 schematically illustrates an endoscope light-source device as a comparative example that substantially collimates laser light from a semiconductor laser light source.
Figure 6:
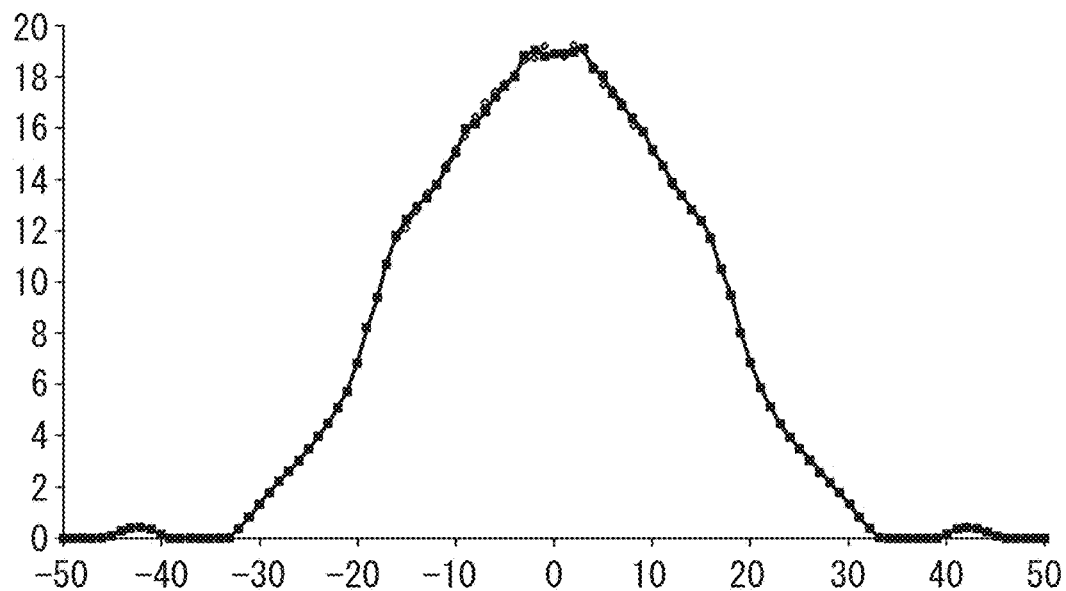
FIG. 6 illustrates a light distribution of illumination light emitted from the light source device in FIG. 5.
Figure 7:
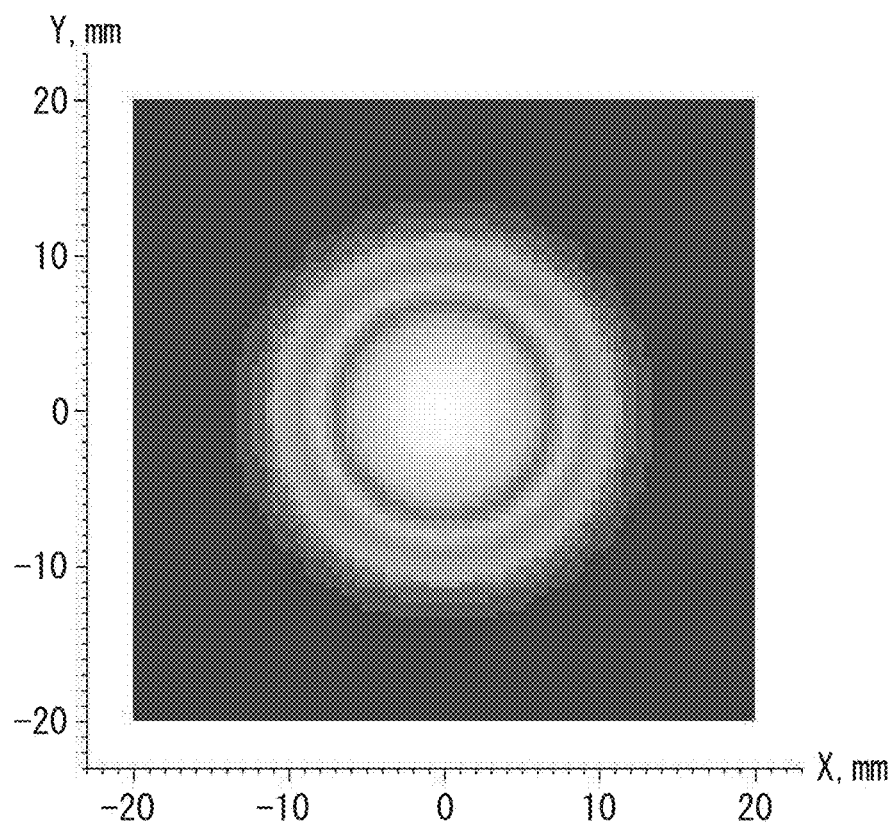
FIG. 7 illustrates an intensity distribution of illumination light between lenses in FIG. 5.

As shown in FIG. 5, in a critical illumination system 10 as a comparative example in which the first lens group 3 is constituted of a collimating lens and that uses the second lens group 4 to focus laser light converted into substantially collimated light, the intensity distribution of the collimated light directly serves as the light distribution of illumination light to be output from the light guide 5. Because the light distribution of the semiconductor laser light source 2 is extremely narrow, as shown in FIG. 2, the light distribution of the illumination light is also narrower than that in this embodiment in FIG. 3, as shown in FIG. 6. As shown in FIG. 7, the intensity distribution of the illumination light in the XY directions is also narrower than that in this embodiment shown in FIG. 4.

This embodiment is advantageous in that, by satisfying conditional expression (1), an increase in size of the device can be prevented, and a decrease in light quantity can be prevented.

In order to prevent an increase in size of a lens, the diameter thereof needs to be 50 mm or smaller. On the other hand, if a lens has a diameter of 10 mm or smaller, the lens would have a short focal length and be vulnerable to variations, thus leading to a decrease in light quantity. It is desirable that a beam a of the most-peripheral laser light have a diameter ranging between 10 mm and 50 mm inclusive.

Assuming that the focal length of the first lens group 3 is defined as f, the NA of the semiconductor laser light source 2 is defined as NAI, and the beam diameter is defined as a, conditional expression (1) is derived from the following:

$$NAI = a/2f, \text{ that is, } a = 2fNAI,$$

and hence, $$10 \leq 2fNAI \leq 50$$

By satisfying conditional expression (2), the low-NA laser light component can be diverged, and the high-NA laser light component can be converged or collimated.

With the second lens group 4 satisfying conditional expression (3), it is advantageous in that the laser light can be efficiently introduced to the light guide 5.

Examples

Figure 8:
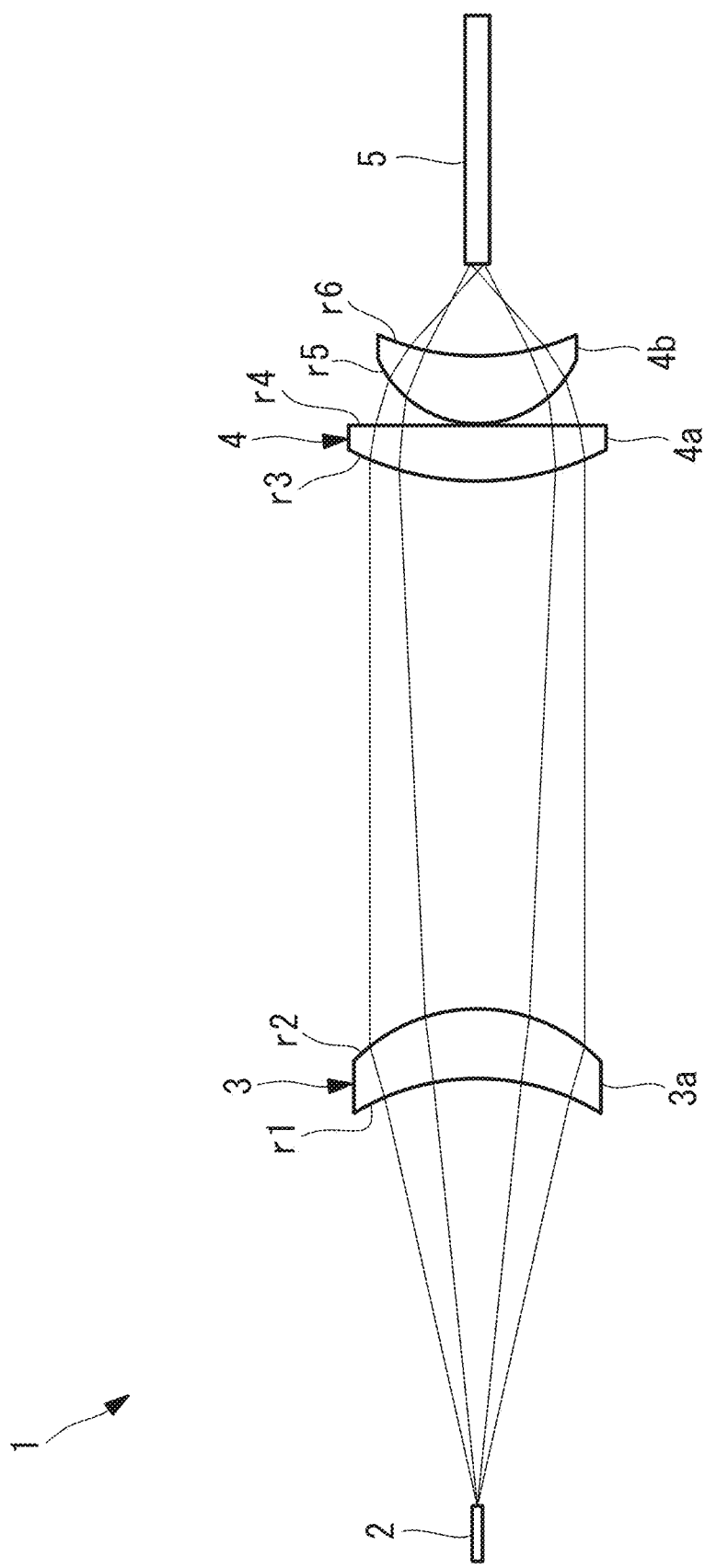
FIG. 8 illustrates a lens arrangement according to a first example of the endoscope light-source device in FIG. 1.

A first example of the endoscope light-source device 1 according to this embodiment will be described below with reference to a lens arrangement in FIG. 8 and lens data indicated below.

The endoscope light-source device 1 according to this example includes the first lens group 3 constituted of a meniscus lens (aspherical lens) 3a having a concave surface disposed facing the semiconductor laser light source 2, and also includes the second lens group 4 constituted of, in the following order from the semiconductor laser light source 2 side, a plano-convex lens 4a having a convex surface disposed facing the semiconductor laser light source 2 and a meniscus lens 4b having a convex surface disposed facing the semiconductor laser light source 2.

A second surface is an aspherical surface expressed with expression (4) indicated below, and the coefficients are as follows. In the lens data, r denotes the radius of curvature, d denotes the distance, nd denotes the refractive index at the d-line, and vd denotes the Abbe number at the d-line, and an aspherical surface Z is derived from expression (4) indicated below:

$$Z = cs^2/(1+\sqrt{(1-(K+1)c^2s^2)}) + As^2 + Bs^4 + Cs^6 + Ds^8 + Es^{10} \tag{4}$$

where
- c: curvature of surface
- s: height from optical axis
- K: conic constant
- A: second-order aspherical coefficient
- B: fourth-order aspherical coefficient
- C: sixth-order aspherical coefficient
- D: eighth-order aspherical coefficient
- E: tenth-order aspherical coefficient First Lens Group and Second Lens Group

| Surface No. | r | d | nd | vd |
|---|---|---|---|---|
| 1 | −34.9224 | 10.0000 | 1.51805 | 64.14 |
| 2 | −32.7180 | 75.0000 | | |
| 3 | 37.0230 | 8.0000 | 1.64100 | 55.38 |
| 4 | ∞ | 0.5000 | | |
| 5 | 15.4350 | 9.5000 | 1.64100 | 55.38 |
| 6 | 35.8750 | 12.9000 | | |

$K = -1.0000$
$A = 0$
$B = -4.4765 \times 10^{-5}$
$C = 1.4192 \times 10^{-7}$
$D = -4.9935 \times 10^{-10}$
$E = 5.7685 \times 10^{-13}$ According to this example,
$\varphi 1 = 0.00255$
$\varphi 2 = 0.0144$
$\varphi 3 = 0.044$
$NA = 0.22$
$NA' = 0.68$
$L = 101.956$
$NA/\varphi 2 = 15.28$
$1/\varphi 1 = 392.16$
$1/\varphi 2 = 69.44$
$NA'/\varphi 3 = 15.45$ whereby conditional expressions (1), (2), and (3) are satisfied.

Figure 9:
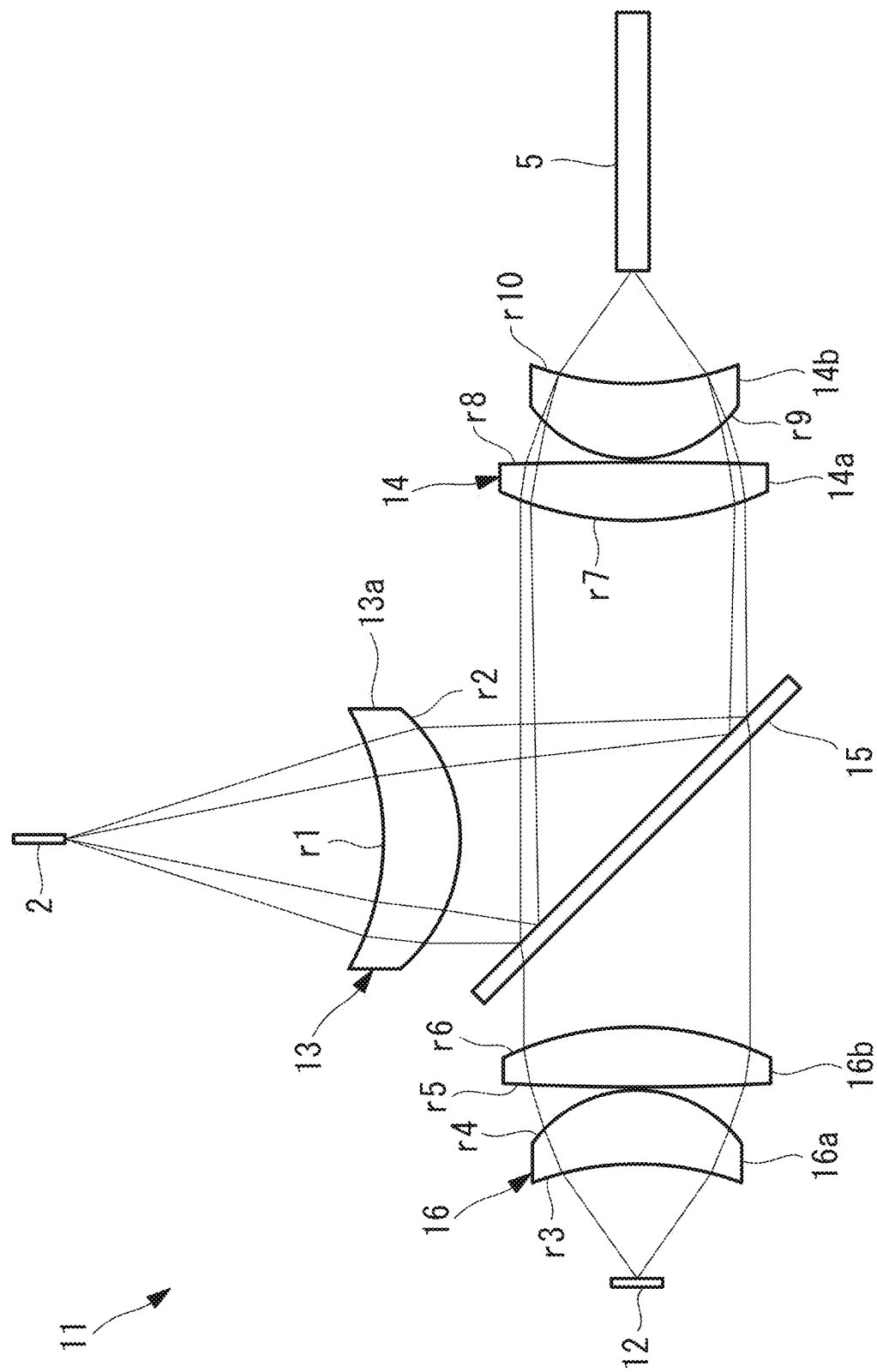
FIG. 9 illustrates a lens arrangement according to a second example having a combination of the endoscope light-source device in FIG. 1 and a light emitting diode.

A second example of an endoscope light-source device 11 according to this embodiment will be described below with reference to a lens arrangement in FIG. 9 and lens data indicated below.

The endoscope light-source device 11 according to this example multiplexes laser light from the semiconductor laser light source 2 and illumination light from a light emitting diode 12 and outputs the multiplexed light. The endoscope light-source device 11 has a dichroic mirror 15 disposed between a first lens group 13 and a second lens group 14 and uses the dichroic mirror 15 to multiplex illumination light, emitted from the light emitting diode 12 and substantially collimated by a collimating lens 16, with illumination light from the semiconductor laser light source 2.

The first lens group 13 is a meniscus lens (aspherical lens) 13a having a concave surface disposed facing the semiconductor laser light source 2, and has a second surface that is an aspherical surface expressed with expression (4).

The collimating lens 16 is constituted of, in the following order from the semiconductor laser light source 2 side, a meniscus lens 16a having a concave surface disposed facing the semiconductor laser light source 2 and a biconvex lens 16b.

The second lens group 14 is constituted of, in the following order from the semiconductor laser light source 2 side, a plano-convex lens 14a having a convex surface disposed facing the semiconductor laser light source 2 and a meniscus lens 14b having a convex surface disposed facing the semiconductor laser light source 2.

First Lens Group

| Surface No. | r | d | nd | vd |
|---|---|---|---|---|
| 1 | −23.2816 | 6.6667 | 1.51805 | 64.14 |
| 2 | −21.812 | | | |

$K = -1.0000$
$A = 0$
$B = -1.51 \times 10^{-4}$
$C = 1.08 \times 10^{-6}$
$D = -8.53 \times 10^{-9}$
$E = 2.22 \times 10^{-11}$ Collimating Lens

| Surface No. | r | d | nd | vd |
|---|---|---|---|---|
| 3 | −26.702 | 6.67 | 1.71582 | 53.87 |
| 4 | −11.4887 | 0.33 | | |
| 5 | 280.7927 | 5.33 | 1.71582 | 53.87 |
| 6 | −28.07 | | | |

Second Lens Group

| Surface No. | r | d | nd | vd |
|---|---|---|---|---|
| 7 | 28.07 | 5.33 | 1.71582 | 53.87 |
| 8 | −280.7927 | 0.33 | | |
| 9 | 11.4887 | 6.67 | 1.71582 | 53.87 |
| 10 | 26.702 | | | |

Figure 10:
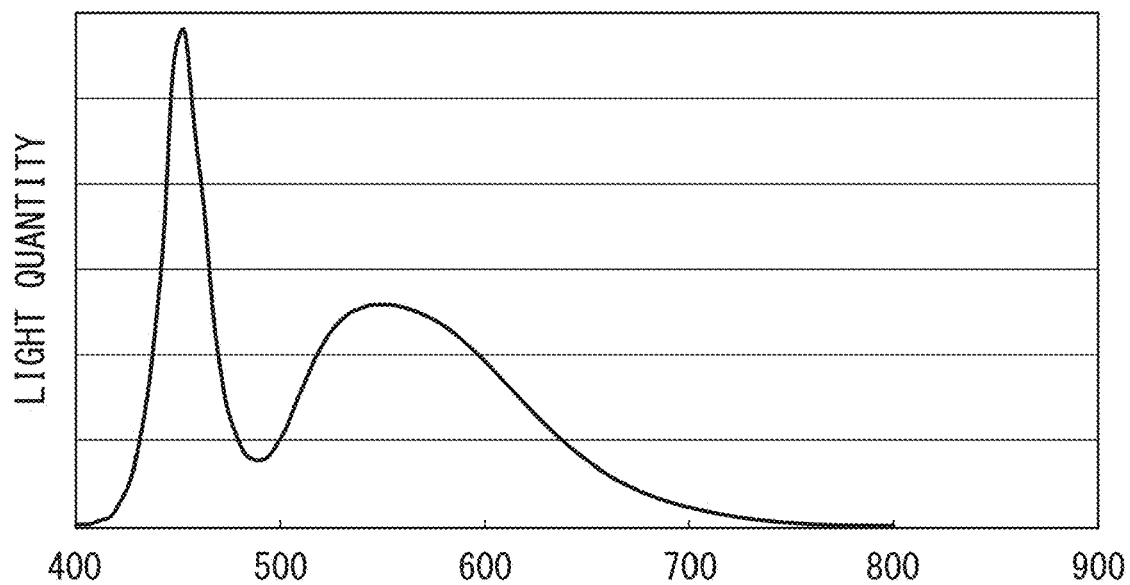
FIG. 10 illustrates a wavelength characteristic of illumination light emitted from the light emitting diode in FIG. 9.
Figure 11:
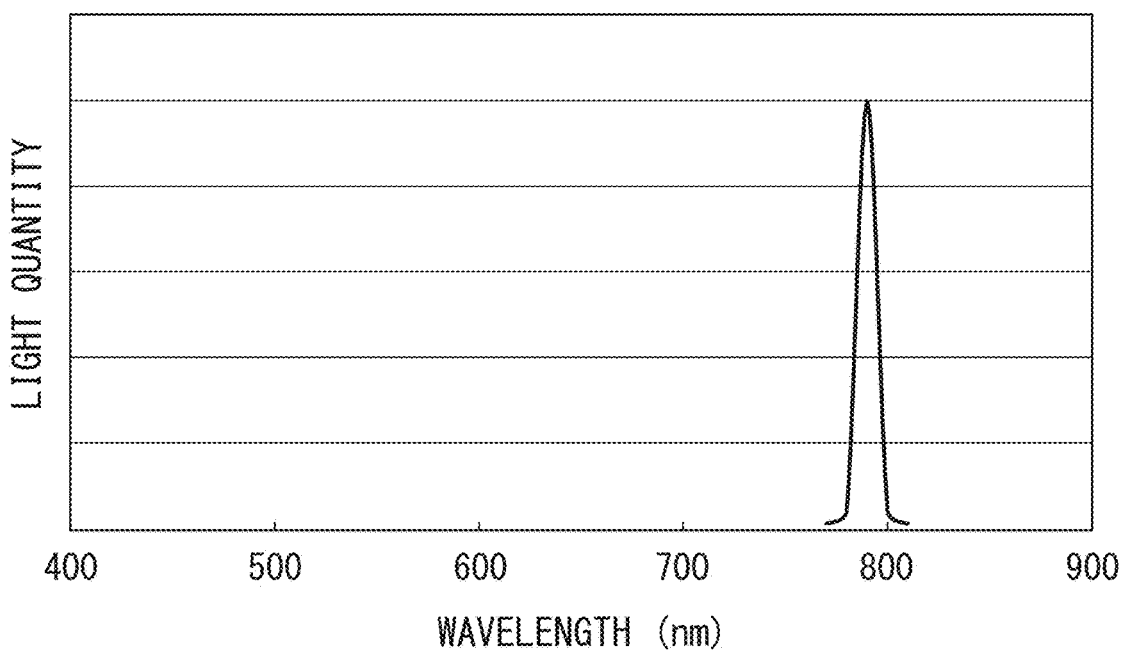
FIG. 11 illustrates a wavelength characteristic of laser light emitted from a semiconductor laser light source in FIG. 9.
Figure 12:
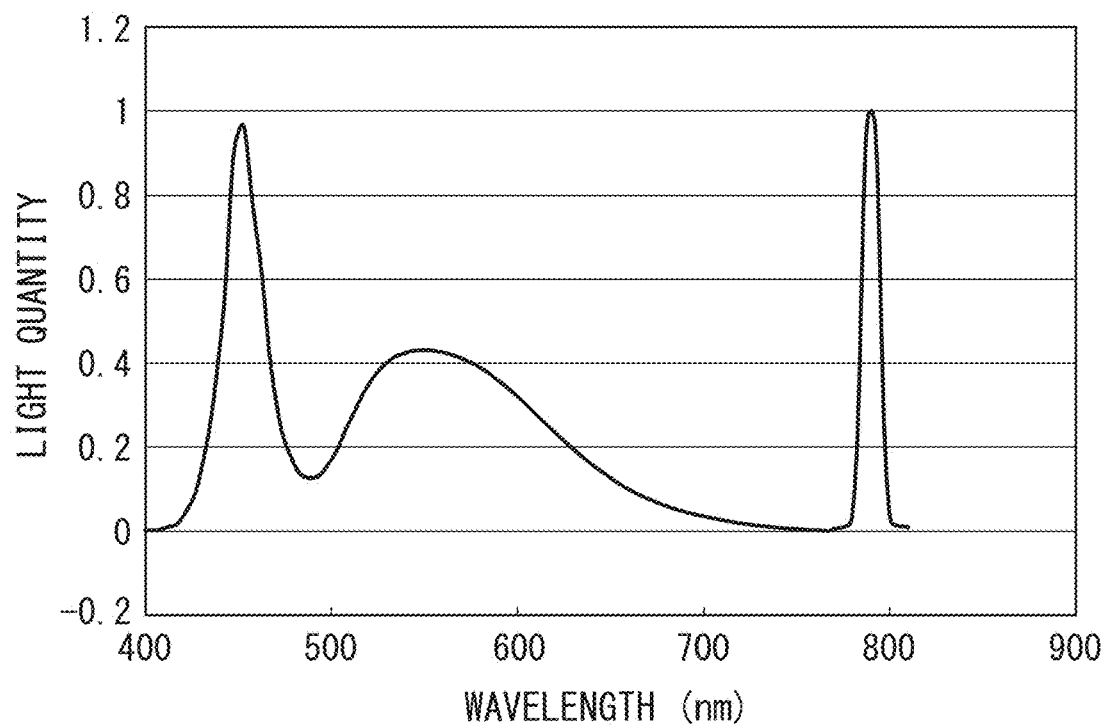
FIG. 12 illustrates a wavelength characteristic of illumination light multiplexed by a dichroic mirror in FIG. 9 and output from the distal end of a light guide.

FIG. 10 illustrates a wavelength characteristic of illumination light emitted from the light emitting diode 12. FIG. 11 illustrates a wavelength characteristic of laser light emitted from the semiconductor laser light source 2. FIG. 12 illustrates a wavelength characteristic of multiplexed illumination light output from the distal end of the light guide 5.

Figure 13:
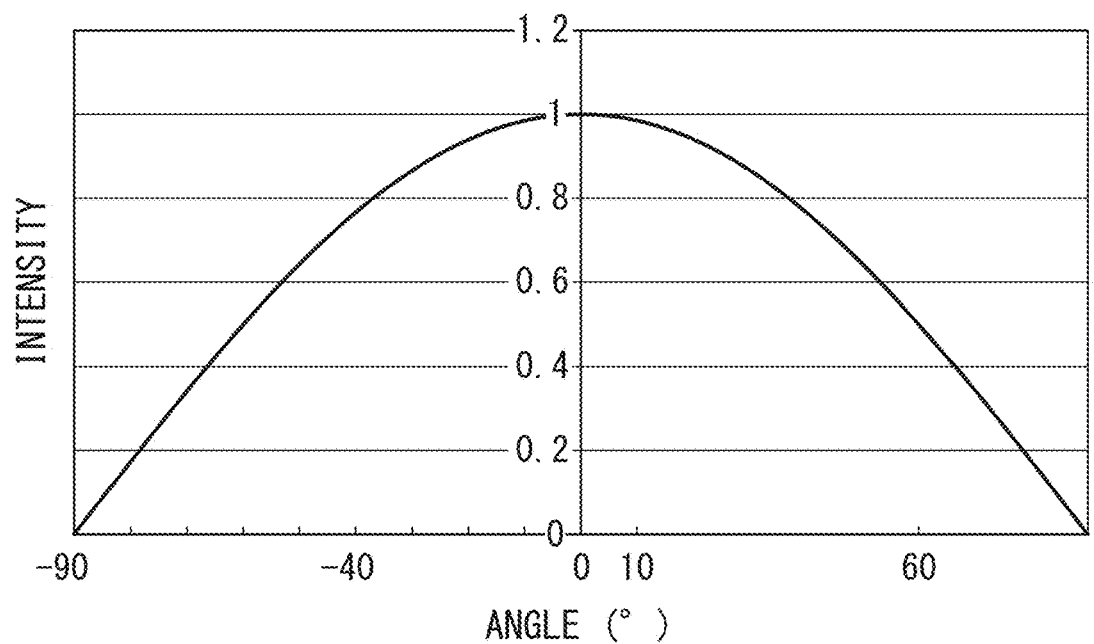
FIG. 13 illustrates a light distribution of illumination light emitted from the light emitting diode in FIG. 9.
Figure 14:
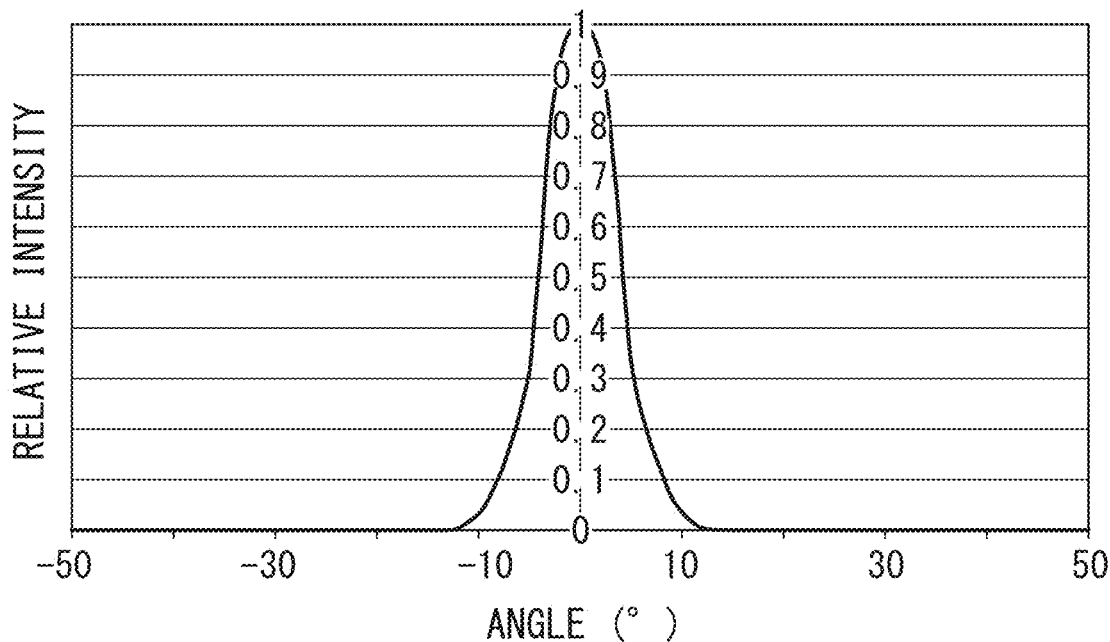
FIG. 14 illustrates a light distribution of laser light emitted from the semiconductor laser light source in FIG. 9.
Figure 15:
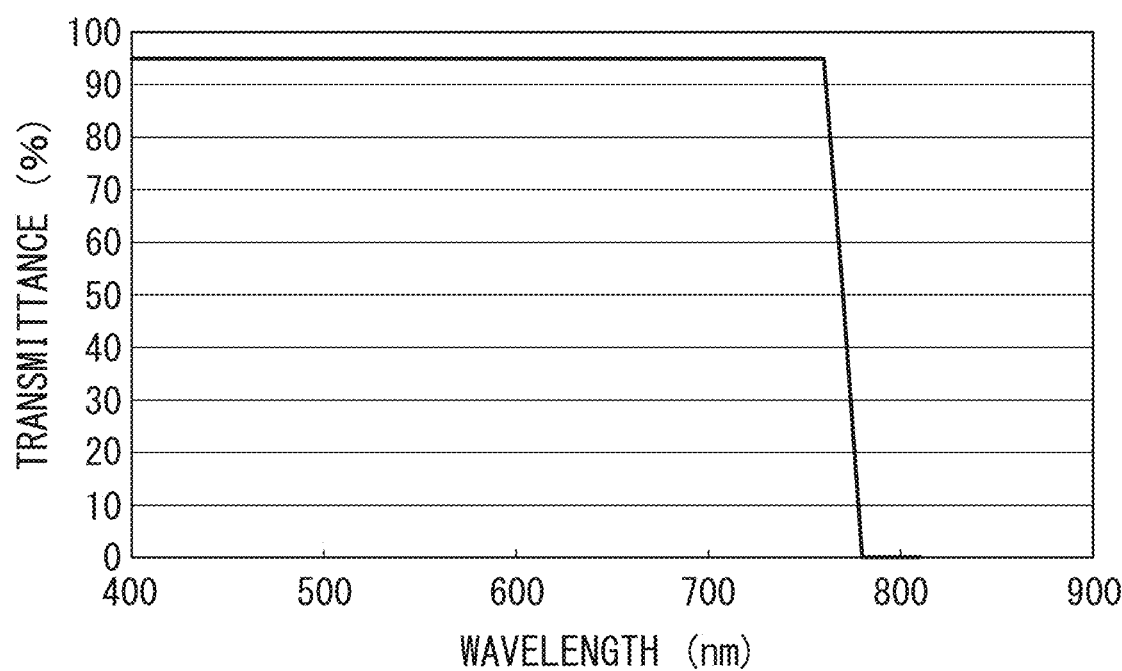
FIG. 15 illustrates a transmittance characteristic of a dichroic mirror in FIG. 9.
Figure 16:
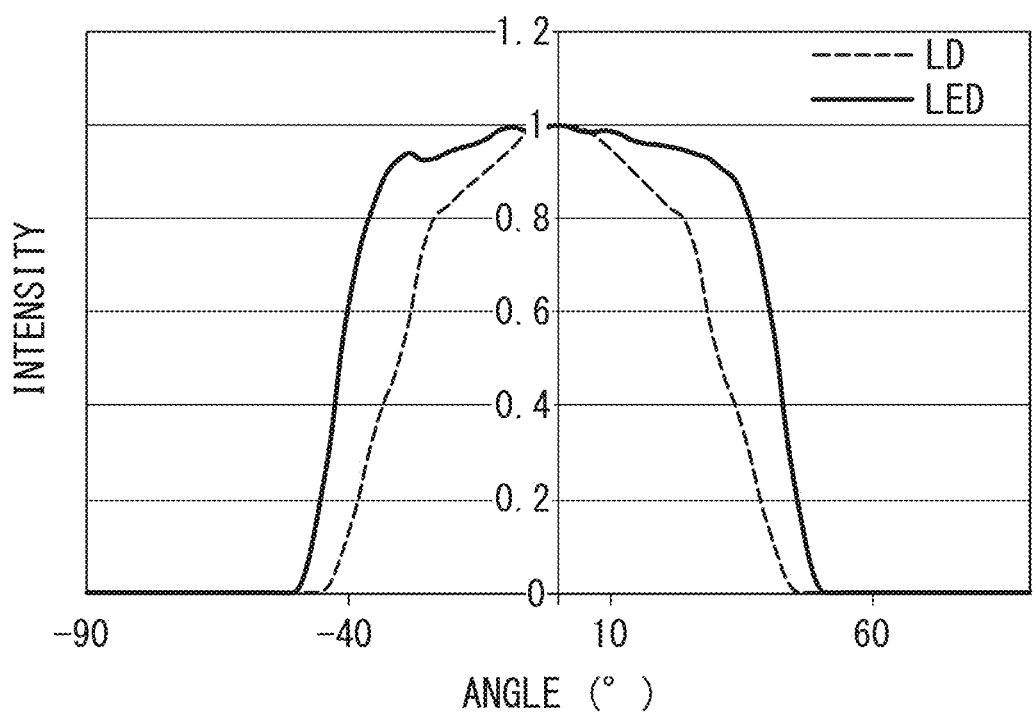
FIG. 16 illustrates a light distribution of illumination light multiplexed by the dichroic mirror in FIG. 9 and output from the distal end of the light guide.

FIG. 13 illustrates a light distribution of illumination light emitted from the light emitting diode 12. FIG. 14 illustrates a light distribution of laser light emitted from the semiconductor laser light source 2. FIG. 15 illustrates a transmittance characteristic of the dichroic mirror 15. FIG. 16 illustrates a light distribution of multiplexed illumination light output from the distal end of the light guide 5. Accordingly, it is clear that the laser light emitted from the semiconductor laser light source 2 has a light distribution similar to that of the illumination light emitted from the light emitting diode 12.

According to this example,
$\varphi 1 = 0.0037$
$\varphi 2 = 0.0215$
$\varphi 3 = 0.0678$
$NA = 0.22$
$NA' = 0.68$
$L = 68.28$
$NA/\varphi 2 = 10.23$
$1/\varphi 1 = 270.27$
$2/\varphi 2 = 46.51$
$NA'/\varphi 3 = 10.03$ whereby conditional expressions (1), (2), and (3) are satisfied.

Figure 17:
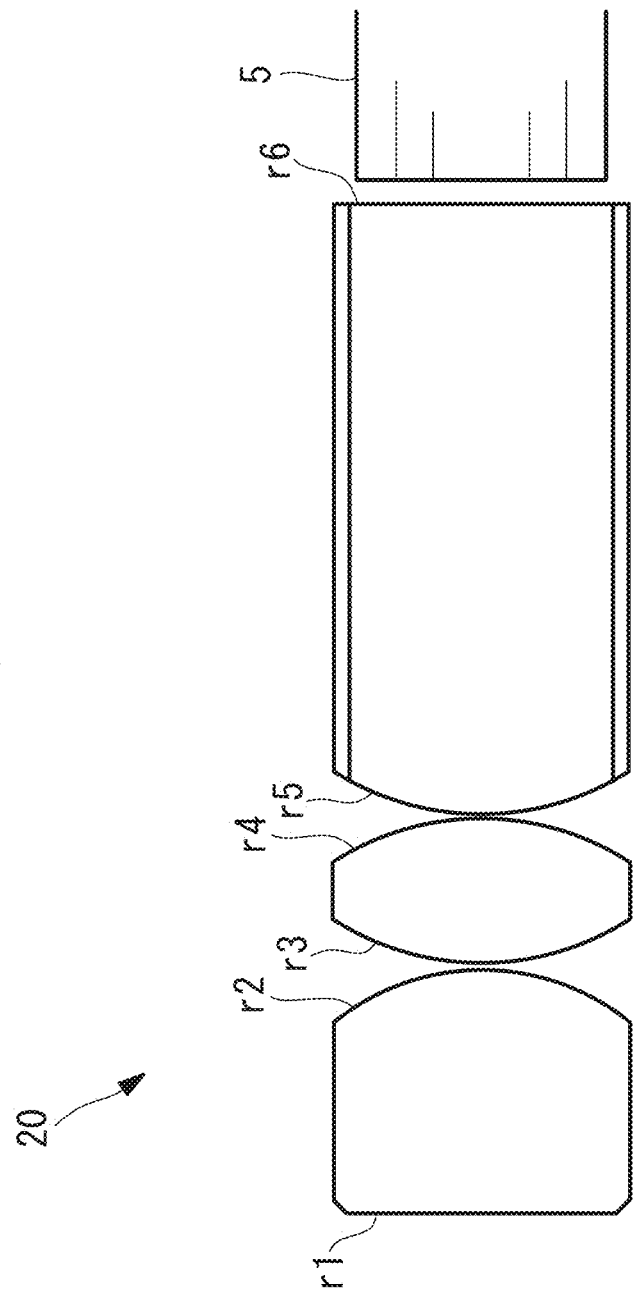
FIG. 17 illustrates an example of an illumination optical system disposed at the distal end of the light guide in FIG. 9.
Figure 18:
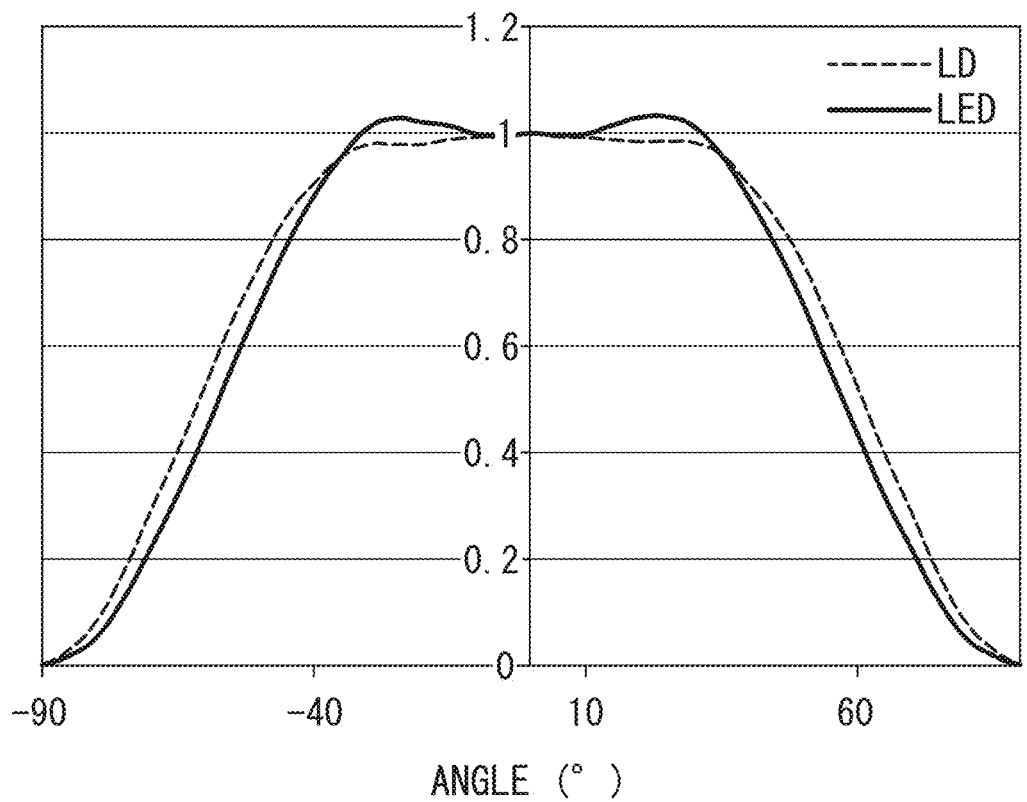
FIG. 18 illustrates a light distribution of laser light emitted from the semiconductor laser light source and a light distribution of illumination light emitted from the light emitting diode in a case where the illumination optical system in FIG. 17 is used.

Furthermore, by disposing an illumination optical system 20 indicated in the Publication of Japanese Patent No. 5897224 at the distal end of the light guide 5, as shown in FIG. 17, the light distribution of the laser light emitted from the semiconductor laser light source 2 can be made more similar to the light distribution of the illumination light emitted from the light emitting diode 12, as shown in FIG. 18.

The lens data of the illumination optical system 20 in FIG. 17 is as follows.

| Surface No. | r | d | nd |
|---|---|---|---|
| 1 | ∞ | 1.00 | 1.888 |
| 2 | −1.60 | 0.03 | |
| 3 | 1.60 | 0.60 | 1.888 |
| 4 | −1.60 | 0.04 | |
| 5 | 1.50 | 2.50 | 1.734 |
| 6 | ∞ | | |

Figure 19:
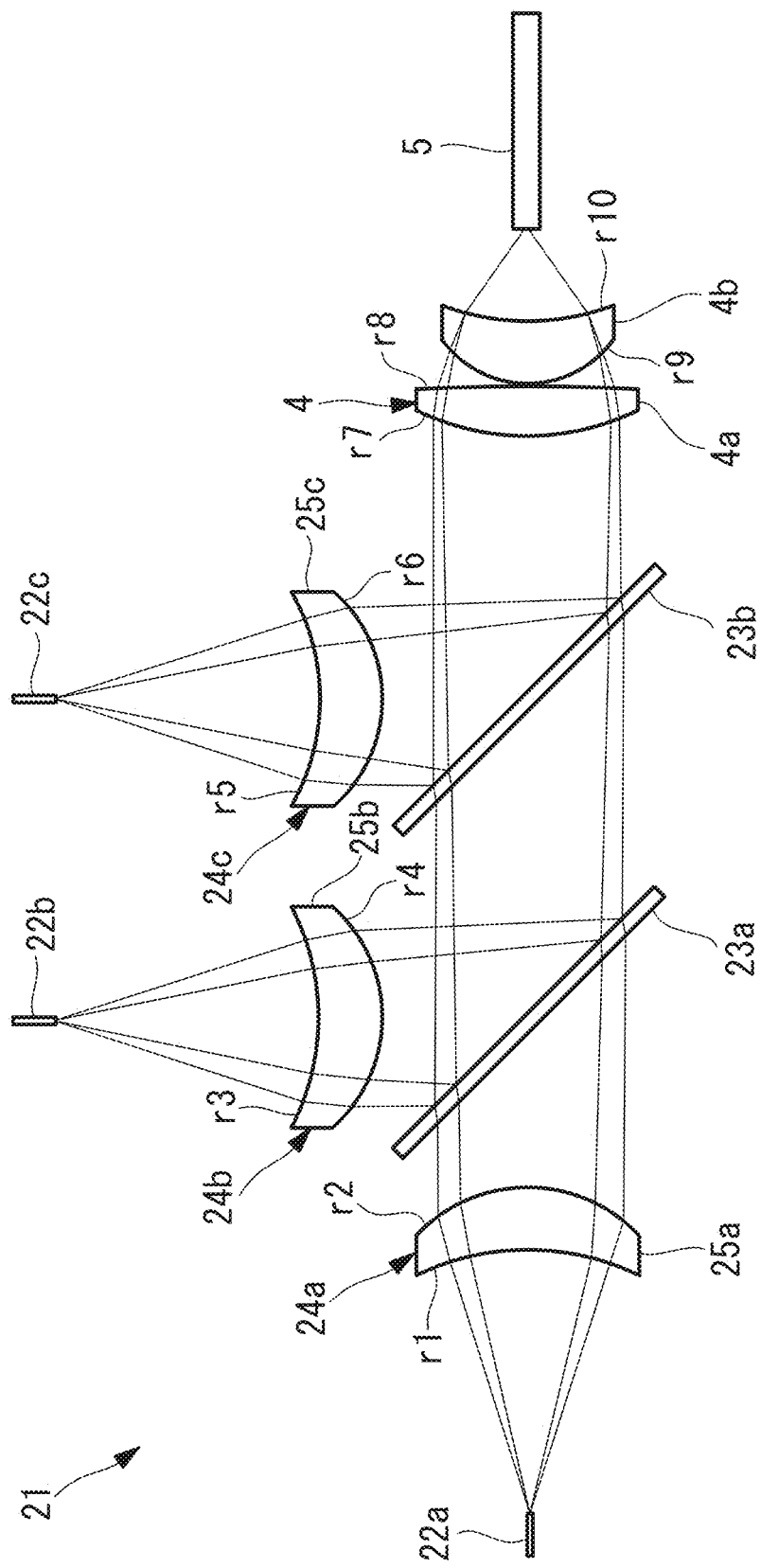
FIG. 19 illustrates a lens arrangement according to a third example of the endoscope light-source device in FIG. 1.

A third example of an endoscope light-source device 21 according to this embodiment will be described below with reference to a lens arrangement in FIG. 19 and lens data indicated below.

The endoscope light-source device 21 according to this example multiplexes laser beams from three semiconductor laser light sources 22a, 22b, and 22c by means of two dichroic mirrors 23a and 23b.

Three first lens groups 24a, 24b, and 24c that allow the laser beams from the three semiconductor laser light sources 22a, 22b, and 22c to pass therethrough are meniscus lenses (aspherical lenses) 25a, 25b, and 25c having concave surfaces disposed facing the semiconductor laser light sources 22a, 22b, and 22c, respectively, and each have a second surface that is an aspherical surface expressed with expression (4). The first group of the first lens groups, that is, the first lens group 24a that allows the laser beam from the first semiconductor laser light source 22a to pass therethrough, and the second group of the first lens groups, that is, the lens group 24b that allows the laser beam from the second semiconductor laser light source 22b to pass therethrough, have the same lens data.

It is desirable that the radius of curvature of each aspherical surface decrease with increasing optical length. Accordingly, a decrease in transmission efficiency can be prevented.

First and Second Groups of First Lens Groups

| Surface No. | r | d | nd | vd |
|---|---|---|---|---|
| 1, 3 | −39.0644 | 10 | 1.51805 | 64.14 |
| 2, 4 | −26.0467 | | | |

$K = -1.0000$
$A = 0$
$B = -1.84 \times 10^{-5}$
$C = -4.13 \times 10^{-8}$
$D = 2.89 \times 10^{-10}$
$E = -5.87 \times 10^{-13}$ Third Group of First Lens Groups

| Surface No. | r | d | nd | vd |
|---|---|---|---|---|
| 5 | −39.9224 | 10 | 1.51805 | 64.14 |
| 6 | −32.718 | | | |

$K = -1.0000$
$A = 0$
$B = -4.48 \times 10^{-5}$
$C = 1.42 \times 10^{-7}$
$D = -4.99 \times 10^{-10}$
$E = 5.77 \times 10^{-13}$ Second Lens Group

| Surface No. | r | d | nd | vd |
|---|---|---|---|---|
| 7 | 42.105 | 8 | 1.71582 | 53.87 |
| 8 | −421.189 | 0.5 | | |
| 9 | 17.233 | 10 | 1.71582 | 53.87 |
| 10 | 40.053 | | | |

Figure 20:
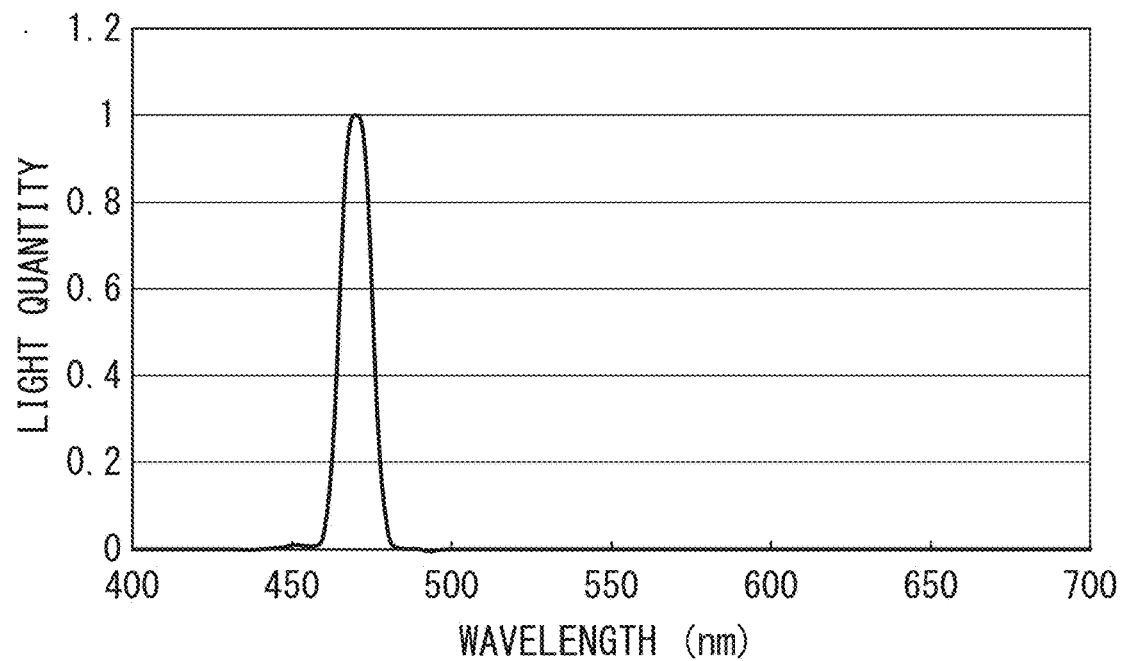
FIG. 20 illustrates a wavelength characteristic of laser light emitted from a first semiconductor laser light source in FIG. 18.
Figure 21:
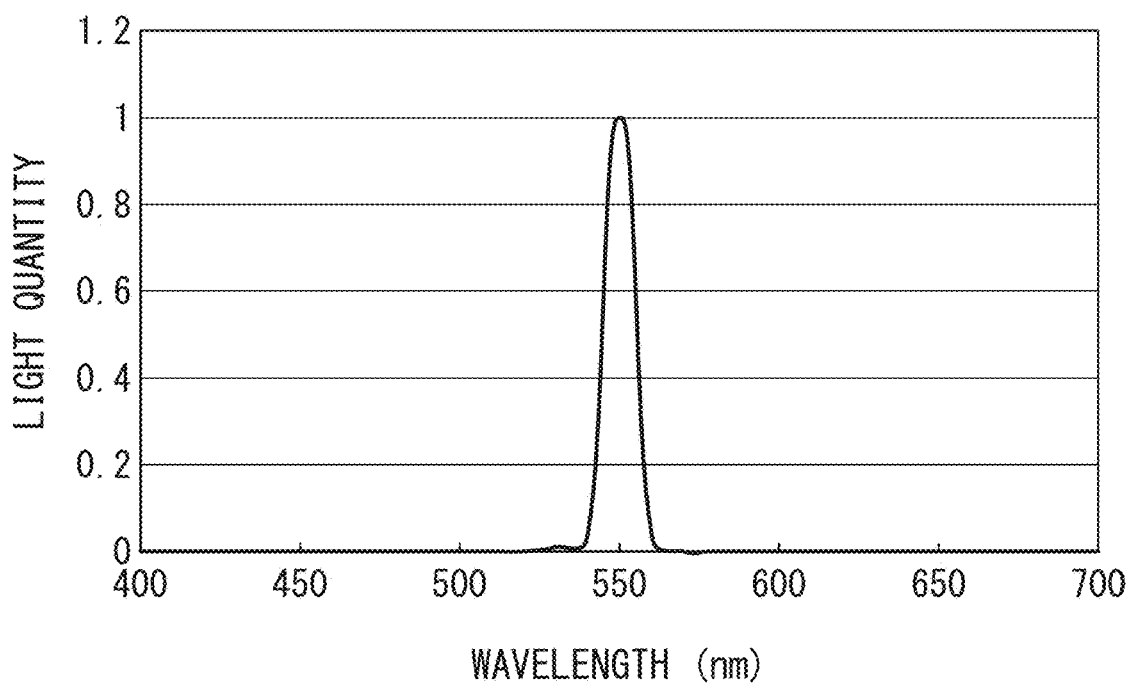
FIG. 21 illustrates a wavelength characteristic of laser light emitted from a second semiconductor laser light source in FIG. 18.
Figure 22:
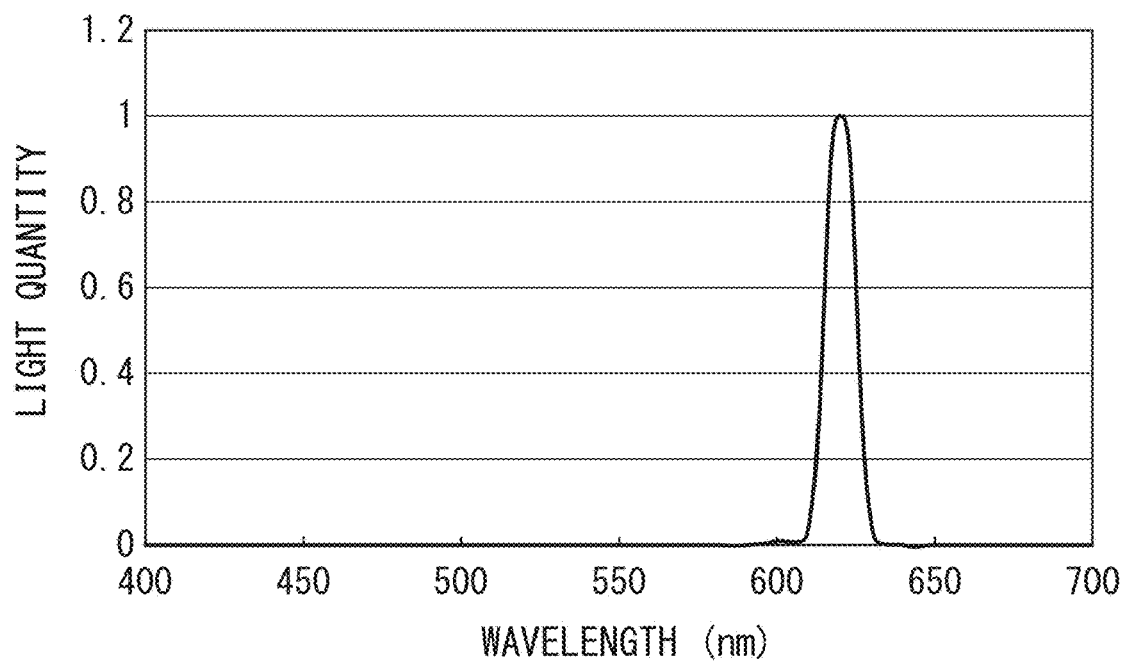
FIG. 22 illustrates a wavelength characteristic of laser light emitted from a third semiconductor laser light source in FIG. 18.
Figure 23:
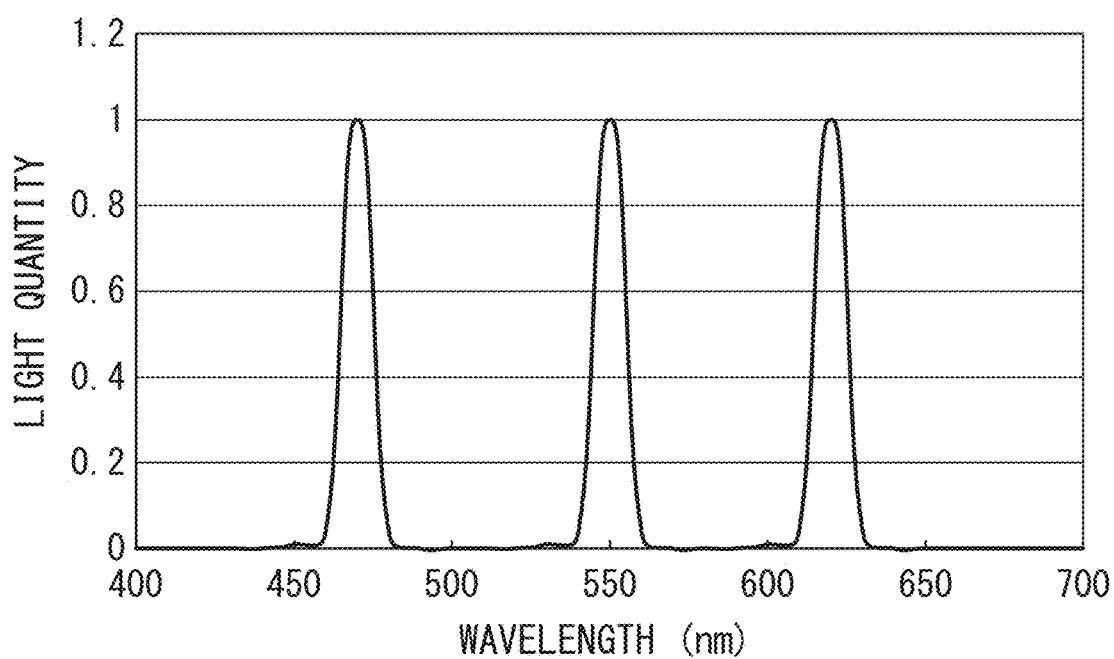
FIG. 23 illustrates a wavelength characteristic of laser light obtained by multiplexing the beams of laser light in FIGS. 20, 21, and 22.

FIG. 20 illustrates a wavelength characteristic of laser light emitted from the first semiconductor laser light source 22a. FIG. 21 illustrates a wavelength characteristic of laser light emitted from the second semiconductor laser light source 22b. FIG. 22 illustrates a wavelength characteristic of laser light emitted from the third semiconductor laser light source 22c. FIG. 23 illustrates a wavelength characteristic of multiplexed illumination light output from the distal end of the light guide 5.

Figure 24:
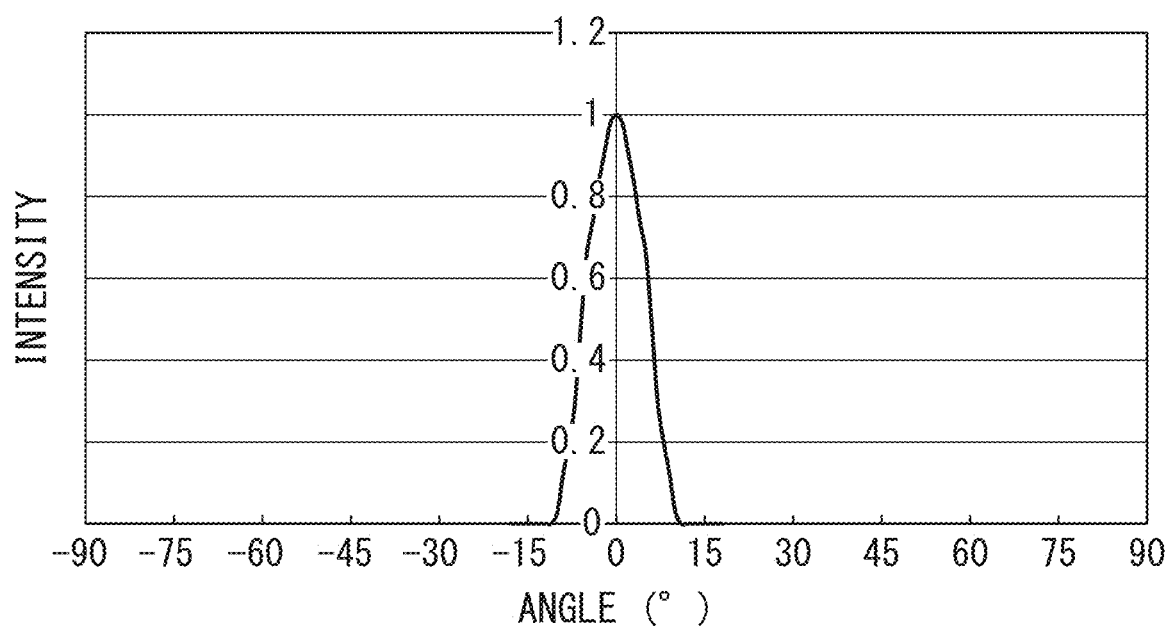
FIG. 24 illustrates a light distribution of the laser light in FIG. 20.
Figure 25:
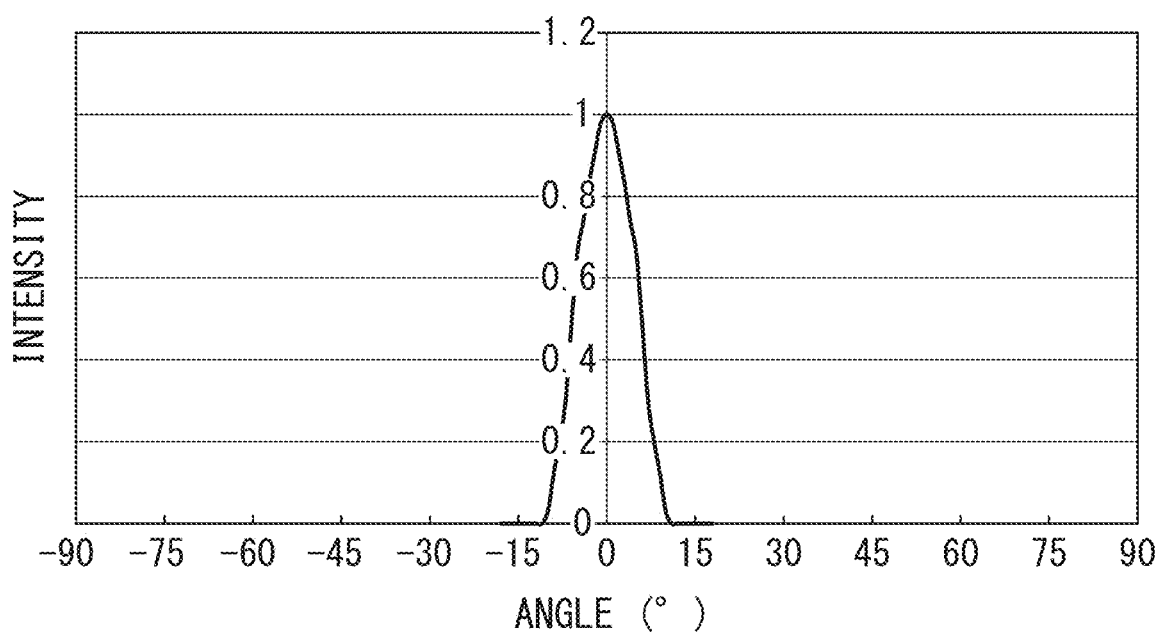
FIG. 25 illustrates a light distribution of the laser light in FIG. 21.
Figure 26:
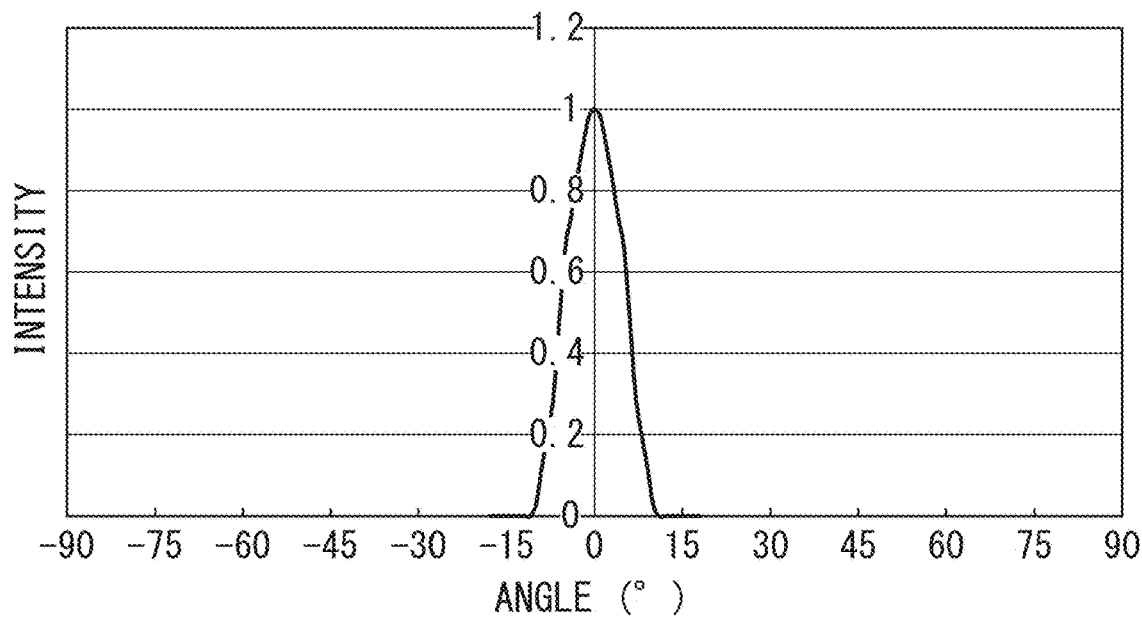
FIG. 26 illustrates a light distribution of the laser light in FIG. 22.
Figure 27:
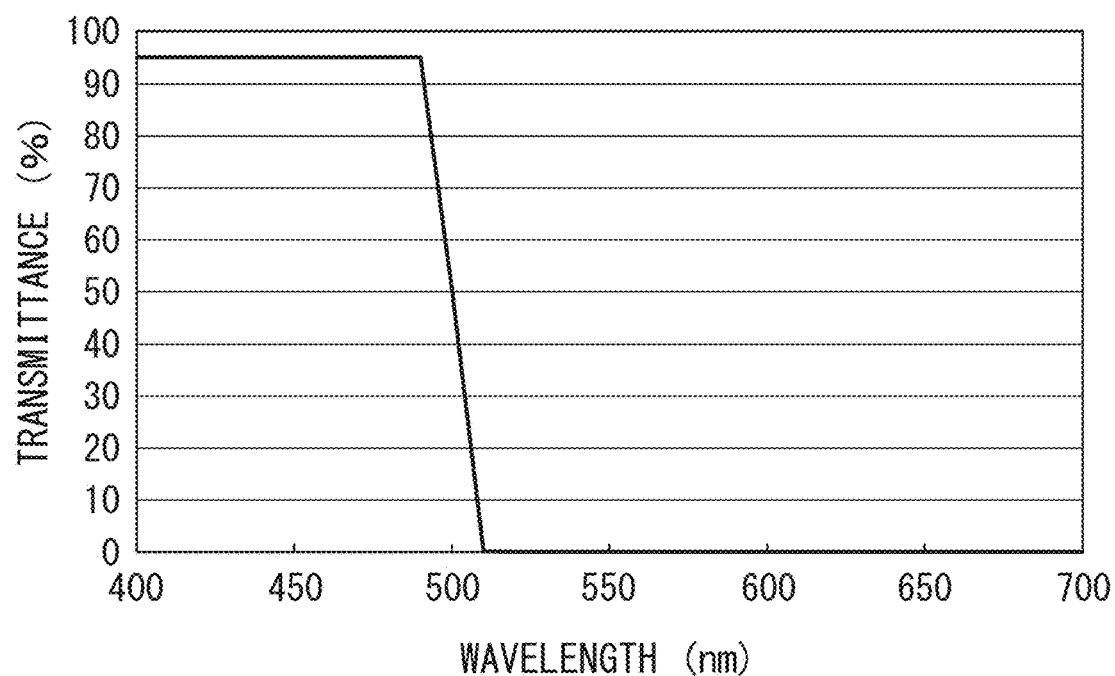
FIG. 27 illustrates a transmittance characteristic of a first dichroic mirror in FIG. 19.
Figure 28:
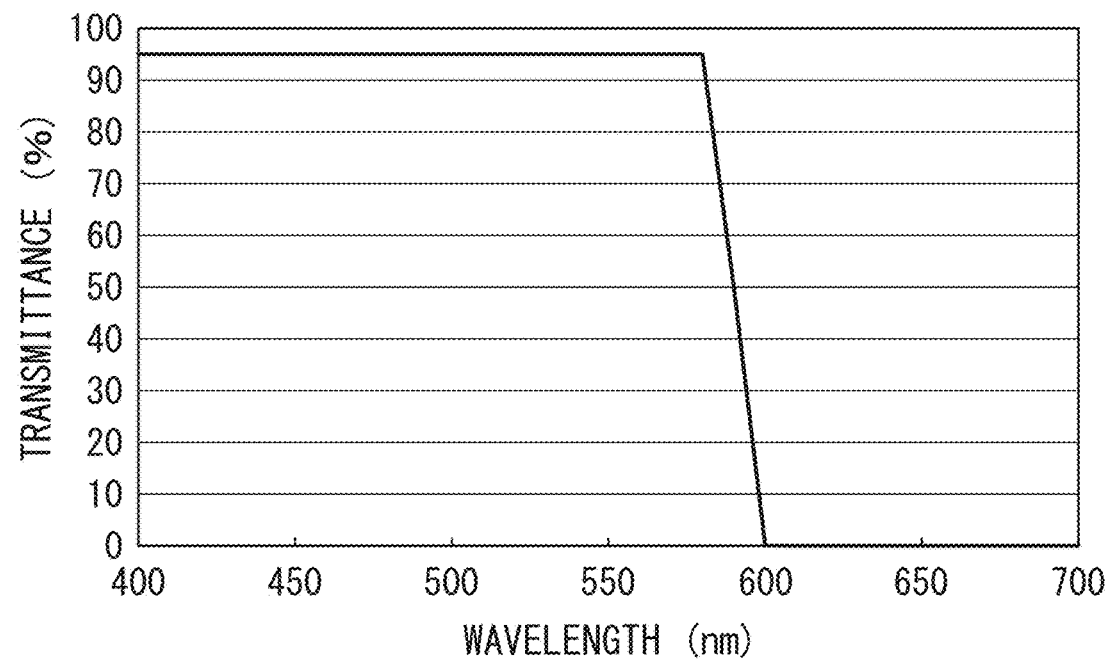
FIG. 28 illustrates a transmittance characteristic of a second dichroic mirror in FIG. 19.
Figure 29:
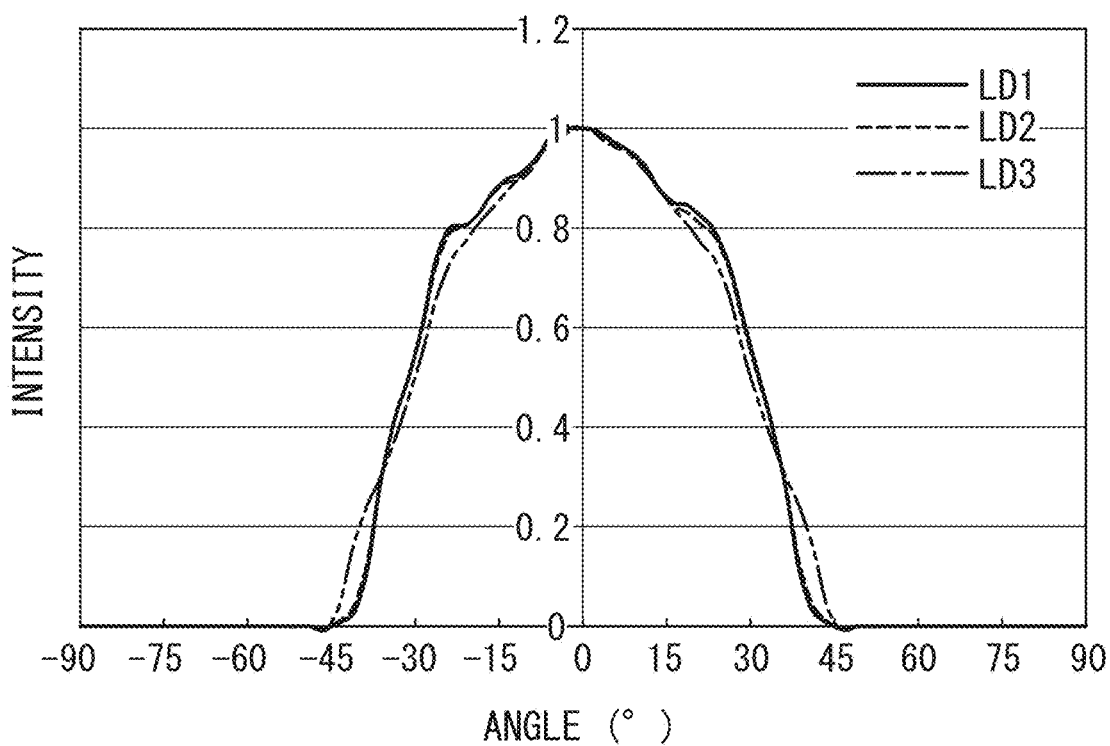
FIG. 29 illustrates a light distribution of laser light output from the distal end of the light guide as a result of the beams of laser light in FIGS. 20, 21, and 22 being multiplexed by means of the dichroic mirrors in FIGS. 27 and 28.

FIG. 24 illustrates a light distribution of laser light emitted from the first semiconductor laser light source 22a. FIG. 25 illustrates a light distribution of laser light emitted from the second semiconductor laser light source 22b. FIG. 26 illustrates a light distribution of laser light emitted from the third semiconductor laser light source 22c. FIG. 27 illustrates a transmittance characteristic of the first dichroic mirror 23a. FIG. 28 illustrates a transmittance characteristic of the second dichroic mirror 23b. FIG. 29 illustrates a light distribution of multiplexed illumination light output from the distal end of the light guide 5. Accordingly, it is clear that the laser beams emitted from the three semiconductor laser light sources 22a, 22b, and 22c have wide light distributions that are similar to one another.

According to this example, in the optical path extending through the first group 24a of the first lens groups and the optical path extending through the second group 24b of the first lens groups, $\varphi1=0.0084$
$\varphi2=0.0146$
$\varphi3=0.046$
NA=0.22
NA'=0.68
L=76.66
NA/$\varphi2$=15.07
1/$\varphi1$=119.05
2/$\varphi2$=68.49
NA'/$\varphi3$=14.78 whereby conditional expressions (1), (2), and (3) are satisfied.

In the optical path extending through the third group 24c of the first lens groups, $\varphi1=0.00255$
$\varphi2=0.0144$
$\varphi3=0.046$
NA=0.22
NA'=0.68
L=101.956
NA/$\varphi2$=15.28
1/$\varphi1$=392.16
2/$\varphi2$=69.44
NA'/$\varphi3$=14.78 whereby conditional expressions (1), (2), and (3) are satisfied.

In this embodiment, the following aspects can be provided.

An aspect of the present invention provides an endoscope light-source device including a semiconductor laser light source, a first lens group that diverges a low-NA light component of light from the semiconductor laser light source and converges or collimates a high-NA light component of the light from the semiconductor laser light source, and a second lens group that focuses the light passing through the first lens group onto an end surface of the light guide. The first lens group includes at least one aspherical lens.

According to this aspect, of the light emitted from the semiconductor laser light source, the low-NA light component is diverged in the first lens group and is subsequently converged in the second lens group so that the light distribution is expanded, whereas the high-NA light component is converged or collimated in the first lens group and is subsequently converged in the second lens group, so that vignetting can be prevented. Accordingly, a wide light distribution required for endoscopic observation can be obtained while light can be extracted from the LD light source with high efficiency.

In the above aspect, the first lens group may have power at a most peripheral area thereof that is higher than power on an optical axis.

With this configuration, the low-NA light component passing through the first lens group can be diverged, whereas the high-NA light component can be converged or collimated.

In the above aspect, conditional expressions indicated below may be satisfied:

$$5 \text{ mm} \leq NA/\varphi 2 \leq 25 \text{ mm} \quad (1)$$

$$1/\varphi 2 \leq L < 1/\varphi 1 \quad (2)$$

where NA denotes the numerical aperture of the semiconductor laser light source, $\varphi 1$ denotes the power of the first lens group on the optical axis, $\varphi 2$ denotes the power of the first lens group at the most peripheral area, and L denotes the distance between the semiconductor laser light source and a principal point of the first lens group.

A value exceeding the upper limit for conditional expression (1) leads to an increase in size of the device, whereas a value falling below the lower limit leads to vulnerability to variations and to a decrease in light quantity.

By satisfying conditional expression (2), the low-NA light component can be diverged, and the high-NA light component can be converged or collimated.

In the above aspect, the first lens group may be constituted of a single aspherical lens.

With this configuration, the endoscope light-source device can have a simple and inexpensive configuration.

In the above aspect, a conditional expression indicated below may be satisfied:

$$5 \text{ mm} \leq NA'/\varphi 3 \leq 25 \text{ mm} \quad (3)$$

where NA' denotes the numerical aperture of the light guide, and $\varphi 3$ denotes the power of the second lens group.

A value exceeding the upper limit for conditional expression (3) leads to an increase in size of the device, whereas a value falling below the lower limit leads to vulnerability to variations and to a decrease in light quantity. Furthermore, by setting the range equivalent to that in conditional expression (1), light can be efficiently introduced to the light guide.

The present invention is advantageous in that it can obtain a wide light distribution required for endoscopic observation while extracting light from an LD light source with high efficiency.

REFERENCE SIGNS LIST 1, 11, 21 endoscope light-source device
2, 22a, 22b, 22c semiconductor laser light source
3, 13, 24a, 24b, 24c first lens group
4, 14 second lens group
5 light guide
3a, 13a, 25a, 25b, 25c meniscus lens (aspherical lens)

The invention claimed is:

1. An endoscope light-source device comprising:
a laser light source;
a first lens group that diverges a low-numerical-aperture light component of light from the laser light source and converges or collimates a high-numerical-aperture light component of the light from the laser light source; and
a second lens group that focuses the light passing through the first lens group onto an end surface of a light guide,
wherein the first lens group includes at least one aspherical lens.

2. The endoscope light-source device according to claim 1,
wherein the first lens group has power at a most peripheral area thereof that is higher than power on an optical axis.

3. The endoscope light-source device according to claim 1,
wherein conditional expressions indicated below are satisfied:

$$5 \text{ mm} \leq NA/\varphi 2 \leq 25 \text{ mm} \quad (1)$$

$$1/\varphi 2 \leq L < 1/\varphi 1 \quad (2)$$

where NA denotes a numerical aperture of the laser light source, $\varphi 1$ denotes power of the first lens group on an optical axis, $\varphi 2$ denotes power of the first lens group at a most peripheral area, and L denotes a distance between the laser light source and a principal point of the first lens group.

4. The endoscope light-source device according to claim 1,
wherein the first lens group is constituted of a single aspherical lens.

5. The endoscope light-source device according to claim 1,
wherein a conditional expression indicated below is satisfied:

$$5 \text{ mm} \leq NA'/\varphi 3 \leq 25 \text{ mm} \quad (3)$$

where NA' denotes a numerical aperture of the light guide, and $\varphi 3$ denotes power of the second lens group.

6. An endoscope system comprising:
the endoscope light-source device according to claim 1; and
an endoscope that includes the light guide.

* * * * *